(12) United States Patent
Alvis et al.

US007119062B1

(10) Patent No.: US 7,119,062 B1
(45) Date of Patent: Oct. 10, 2006

(54) METHODS AND COMPOSITIONS FOR IMPROVED ARTICULAR SURGERY USING COLLAGEN

(75) Inventors: Mark Ray Alvis, Santa Cruz, CA (US); Melissa K. C. Brown, Los Altos, CA (US); Roy C. Fiebiger, Los Gatos, CA (US)

(73) Assignee: Neucoll, Inc., North Bend, WA (US)

( * ) Notice: Subject to any disclaimer, the term of this patent is extended or adjusted under 35 U.S.C. 154(b) by 276 days.

(21) Appl. No.: 10/082,443

(22) Filed: Feb. 22, 2002

Related U.S. Application Data (60) Provisional application No. 60/271,116, filed on Feb. 23, 2001.

(51) Int. Cl.
*A61K 38/00* (2006.01)
*A61K 38/17* (2006.01)
*A61M 29/00* (2006.01)

(52) U.S. Cl. .......................... 514/2; 514/21; 514/963; 530/356; 604/96.01

(58) Field of Classification Search .................. 514/2, 514/21, 963; 530/356; 604/96.01
See application file for complete search history.

(56) References Cited

U.S. PATENT DOCUMENTS

| | | | |
|---|---|---|---|
| 3,949,073 A | 4/1976 | Daniels et al. | |
| 3,966,908 A | 6/1976 | Balassa | |
| 4,140,537 A | 2/1979 | Luck et al. | |
| 4,233,360 A | 11/1980 | Luck et al. | |
| 4,250,139 A | 2/1981 | Luck et al. | |
| 4,391,749 A | 7/1983 | Engvall et al. | |
| 4,424,208 A | 1/1984 | Wallace et al. | |
| 4,473,551 A | 9/1984 | Schinitsky | |
| 4,582,640 A | 4/1986 | Smestad et al. | |
| 4,619,913 A | 10/1986 | Luck et al. | |
| 4,703,108 A | 10/1987 | Silver et al. | |
| 4,704,273 A | 11/1987 | McMichael | |
| 4,760,131 A | 7/1988 | Sundsmo et al. | |
| 4,764,377 A | 8/1988 | Goodson | |
| 4,774,091 A | 9/1988 | Yamahira et al. | |
| 4,789,662 A | 12/1988 | Thomas-Leurquin et al. | |
| 4,804,745 A | 2/1989 | Koepff et al. | |
| 4,855,134 A * | 8/1989 | Yamahira et al. ........... | 424/85.7 |
| 4,865,846 A | 9/1989 | Kaufman | |
| 4,906,670 A | 3/1990 | Higashi et al. | |
| 4,919,939 A | 4/1990 | Baker | |
| 4,923,699 A | 5/1990 | Kaufman | |
| RE33,375 E | 10/1990 | Luck et al. | |
| 5,002,071 A | 3/1991 | Harrell | |
| 5,024,841 A | 6/1991 | Chu et al. | |
| 5,036,056 A | 7/1991 | Kludas | |
| 5,385,738 A | 1/1995 | Yamahira et al. | |
| 5,540,912 A | 7/1996 | Roorda et al. | |
| 5,616,689 A | 4/1997 | Shenoy et al. | |
| 5,639,796 A | 6/1997 | Lee | |
| RE35,748 E | 3/1998 | Luck et al. | |
| 5,760,077 A | 6/1998 | Shahinian, Jr. | |
| 5,766,631 A | 6/1998 | Arnold | |
| 5,902,606 A | 5/1999 | Wunderlich et al. | |
| 5,919,473 A | 7/1999 | Elkhoury | |
| 5,980,946 A | 11/1999 | Jones et al. | |
| 6,083,918 A | 7/2000 | Klaus | |
| 6,087,355 A | 7/2000 | Cho et al. | |
| 6,165,983 A | 12/2000 | Klaus | |
| 6,261,582 B1 | 7/2001 | Needham et al. | |
| 6,316,015 B1 | 11/2001 | Rondelez et al. | |
| 6,316,033 B1 | 11/2001 | Lin | |
| 6,322,592 B1 | 11/2001 | Lucas et al. | |
| 6,350,781 B1 | 2/2002 | Shahinia, Jr. | |
| 6,407,088 B1 | 6/2002 | Dong et al. | |
| 6,645,168 B1 | 11/2003 | Demopulos et al. | |
| 2001/0049366 A1 | 12/2001 | Singh et al. | |
| 2002/0004499 A1 | 1/2002 | Rudnic et al. | |

FOREIGN PATENT DOCUMENTS

| | | |
|---|---|---|
| EP | 338813 | 10/1989 |
| SU | 880426 | 11/1981 |

OTHER PUBLICATIONS

Maeda et al., Journal of Controlled Release, vol. 62, pp. 313-324, 1999.*

Altman, R. D. (1992) "Laboratory Findings in Osteoarthritis" Chapter 12 *In Osteoarthritis: Diagnosis and Medical/Surgical Management*, Moskowitz, Howell, Goldberg and Mankin, Eds., WB Saunders Co., Harcourt Brace Jovanovich, pp. 313-328.

(Continued)

*Primary Examiner*—Jon Weber
*Assistant Examiner*—Abdel A. Mohamed
(74) *Attorney, Agent, or Firm*—Morrison & Foerster LLP (57) ABSTRACT

The invention provides methods for treating post-surgical articular or incisional pain and/or discomfort in a patient. The invention further provides improved surgical methods and controlled release formulations for treating an articular injury of a joint in a patient, in which a collagen formulation is used in conjunction with a surgical procedure to treat the articular injury or the side effects of the surgical procedure. Collagen formulations of the invention and their use, in addition to the surgical procedure, may provide at least one or more of the following benefits: reduced patient pain, shortened recovery time and/or improved joint condition (including treatment of the underlying articular injury). Moreover, the methods and compositions of the invention can be used in conjunction with essentially any surgical procedure used to treat an articular injury. The invention further provides compositions and methods for treating post-surgical articular or incisional pain in a patient as well as a catheter for use in the methods of the invention.

98 Claims, 2 Drawing Sheets

OTHER PUBLICATIONS

Balazs, E.A. and Denlinger, J. L. (1989). "Clinical Uses of Hyaluronan" In *Biology of Hyaluronan* . John Wiley & Sons, 143:265-275.

Batyrov, T.U. et al. (Mar.-Apr. 1982). "Experimental Study of the Local Anesthetic Action of Trimecaine Prolonged with Collagen," *Stomatologiya* 61(2): 7-10. (English Abstract).

Bentz, H. et al. (1998). "Improved Local Delivery of TGF-β2 by Binding to Injectable Fibrillar Collagen Via Difunctional Polyethylene Glycol," *J. Biomed. Mater. Res.* 39:539-548.

Brahn, E. (Apr. 1991). "Animal Models of Rheumatoid Arthritis: Clues to Etiology and Treatment," *Clin. Orthop. and Related Research* . 265:42-53.

Capaldi, M. J. and Chapman, J.A. (1982). "The C-Terminal Extrahelical Peptide of Type I Collagen an Its Role in Fibrillogenesis *In Vitro,*" *Biopolymers* 21:2291-2313.

Carron, H. (Apr. 1978). "Relieving Pain with Nerve Blocks," *Geriatrics* 49-52,57.

Cepeda, M. S. et al. (1997). "Pain Relief After Knee Arthroscopy: Intra-Articular Morphine, Intra-Articular Bupivacaine, or Subcutaneous Morphine," *Reg. Anesth.* 22(3):233-238.

Cooperman, L. et al. (1984). "The Immunogenicity of Injectable Collagen I. a 1-Year Prospective Study," *J. of the Am. Acad. Dermatol.* 10:638-646.

Creamer, P. et al. (1996) "Pain Mechanisms in Osteoarthritis of the Knee: Effect of Intraarticular Anesthetic," The *J. of Rheumatol.* 23:1031-1036.

De Andres, J. et al. (1998). "Intra-Articular Analgesia After Arthroscopic Knee Surgery: Comparison of Three Different Regimens," *Eur. J. of Anaesth.* 15:10-15.

Debruyne, D. et al. (1985). Monitoring Serum Bupivacaïne Levels During Arthroscopy, *Eur. J. of Clin. Pharmacol.* 27:733-735.

DeLustro, F. et al. (1987). "Reaction to Injectable Collagen: Results in Animal Models and Clinical Use," *Plast. Reconstruct. Surg.* 79:581-592.

DeLustro, F. et al. (Jul. 1988). "Immunity to Injectable Collagen and Autoimmune Disease: A Summary of Current Understanding," *Dermatol. Surg. Oncol.* 14(Suppl. 1)(7):57-65.

Frank, D. H. et al. (Jun. 1991). "Human Antibody Response Following Multiple Injections of Bovine Collagen," *Plast. Reconstruct. Surg* 87(6):1080-1088.

Fraser, R. E et al. (Jun. 1993). "The Kinetics of Hyalouronan in Normal and Acutely Inflamed Synovial Joints: Observation With Experimental Arthritis in Sheep," *Sem. Arthritis and Rheumatism* 22(6)( Suppl. 1):9-17.

Frizziero, L et al. (1998). "Intra-Articular Hyaluronic Acid in the Treatment of Osteoarthritis of the Knee: Clinical and Morphological Study," *Clin. and Exp. Rheumatol.* 16:441-449.

Gelman, R. A et al. (Nov. 1979). "Collagen Fibril Formation *In Vitro,*" *J. Biol. Chem.* 254:11741-11745.

Gradinger, R. et al. (Jun. 1995). "Influence of Various Irrigation Fluids on Articular Cartilage," *Arthroscopy: The Journal of Arthroscopic and Related Surgery* 11(3):263-269.

Henderson , R. C. et al. (1990). "Postarthroscopy Analgesia with Bupivacaine: A Prospective, Randomized, Blinded Evaluation," The *Am. J. of Sports Med.* 18(6):614-617.

Horakava, P. Z.et al. (1967). Prolongation Par Les Substances Collagenes De *Therapie* 22(6): 1455-1460. (English Abstract).

Kaeding, C. et al. (1990). "Bupivacaine Use After Knee Arthroscopy: A Pharmacokinetics and Pain Control Study," *Arthroscopy: The Journal of Arthroscopic and Related Surgery* 6(1):33-39.

Konobevtsev , O. et al. (1982). "Local Anesthetic Effect of Trimecaine Prolonged by Collagen," *Stomatologiya* 61(5): 7-9. (English Abstract).

Konobevtsev et al. (1986). "New Drug Forms of the Local Anesthetic Pyormecaine," *Anaesteziol Reanimatol* 0(3): 50-52. (English Abstract).

Kroesen, S. et al. (2000). Induction of an Acute Attack of Calcium Pyrophosphate Dihydrate Arthritis by Intra-Articular Injection of Hylan G-F 20 (Synvisc). *Clin. Rheumatol.* 19:147-149.

Mah, E. T. et al. (1991). "Effects of Irrigation Fluid on Human Menisci: An Experimental Comparison of Water, Normal Saline and Glycine," *The Journal of Arthroscopie and Related Surgery* 7(1):24:32.

Marshall, G. J. et al. (1988). "Synovisol as an Irrigant for Electrosurgery of Joints," *Arthroscopy: The Journal of Arthroscopic and Related Surgery* 4(3):187-193.

Marshall, K.W. et al. (2000). "Amelioration of Disease Severity by Intraarticular Hylan Therapy in Bilateral Canine Osteoarthritis," The *J. of Orthop. Res.* 18:416-425.

McCain, J. P. et al. (1989). "Preliminary Studies on the Use of a Viscoelastic Solution in Arthroscopic Surgery of the Temporomandibular Joint," *J. Oral Maxillofac. Surg.* 47:1161-1168.

McPherson, J. M. et al. (1988). "The Effects of Heparin on the Physicochemical Properties of Reconstituted Collagen," *Coll. Relat. Res.* 8(1):65-82.

Meinig, R. P. et al. (1988). "Plasma Bupivacaine Levels Following Single Dose Intraarticular Instillation for Arthroscopy," *The Am. J. of Sports Med.* 16(3):295-300.

Moya, F. (1981). "Treatment of Osteoarthritis of the Spine and Herpetic Neuralgia at the Pain Center, Mount Sinai Medical Center" *In New Approaches to Treatment of Chronic Pain: A Review of Multidisciplinary Pain Clinics and Pain Centers.* Ng, L. K.Y. ed., 36: 118-121.

Myers, L. K . et al. (1997). "Collagen-Induced Arthritis, An Animal Model of Atoimmunity," *Life Sci.* 61(19):1861-1878.

Noyes, F. R. and Westin-Barber, S. D. (Feb. 1997). "Athroscopic-Assisted Allograft Anterior Cruciate Ligament Reconstruction in Patients With Symptomatic Arthrosis," Arthoroscopy: The Journal of Arthroscopic and Related Surgery 13(1):24-32.

Pavelka, K. et al. (Jun. 1999). "Pain Reduction in Knee Osteoarthritis: A Novel Treatment Using Intra-articular Type I Collagen NeuVisc™ Synovial Fluid Supplement," Presented at *4th Congress of the European Federation of National Associations of Orthapaedics and Traumatology*, Brussels, Belgium. Total pages 2.

Pavelka et al. (Sep. 1999). "Safety Following Intra-articular Injections of NeuVisc™—Two Studies," *Fourth World Congress of the Osteo Arthritis Research Society International*, Vienna, Austria. total pages 2.

Piez, K. (1985). "Collagen", *Encyclopedia of Polymer Science and Engineering: Cellular Materials to Composites.* 2nd Ed., John Wiley & Sons. 3:699-727.

Rodeo, S. A. and Warren, R. F. (Jul. 1996). "Meniscal Repair Using The Outside-To-Inside Technique," *Clin. Sports Med.* 15:469-481.

Rosenblatt, J. et al. (1989). "The Effect of Collagen Fiber Size Distribution on the Release Rate of Proteins from Collagen Matrices by Diffusion," *J. of Controlled Release* 9:195-203.

Rubin, A. L. et al. (Feb. 1965). "Effects of Pepsin Treatment on the Interaction Properties of Tropocollagen Macromolecules," *Biochemistry* 4(2):181-190.

Shroeder-Tefft, J. A et al. (1997). "Collagen and Heparin Matrices for Growth Factor Delivery," *Controlled Release* 49:291-298.

Smith, I. et al. (1991). "Effects of Local Anesthesia on Recovery After Outpatient Arthroscopy," *Anesth. Analg.* 73:536-539.

Solanki, D.R. et al. (1992). "Serum Bupivacaine Concentrations After Intraarticular Injection for Pain Relief After Knee Arthroscopy," *Arthroscopy* 8:44-47.

Steffen, C. et al. (1975). "Collagen-Induced Acute Synovitis in Collagen-Immunized Rabbits," *A. Immun.-Forsch. Bd.* 150:432-446.

Summary of Product Characteristics: Chirocaine® (Manufacturer: Abbott): 2 pages total.

Wallace, D. G. et al. (1986). "Multiple Denaturational Transitions in Fibrillar Collagen," *Biopolymers* 25:1875-1893.

Wasudev, G. et al. (1990). "Blood Levels of Bupivacaine After Arthroscopy of the Knee Joint," *Arthroscopy* 6(1):40-42.

Weiss, C. et al. (1986). "The Role of Na-hylan in Reducing Postsurgical Tendon Adhesions," *Bull. Hosp. Jt. Dis. Orthop. Inst.* 46:9-15.

Whately, J. S. et al. (Mar. 2000). "The Effect of an Exogenous Fibrin Clot on the Regeneration of the Triangular Fibrocartilage Complex: An In Vivo Experimental Study in Dogs," *Arthroscopy* 16:127-136.

Olsen, D. et al. (2003). "Recombinant Collagen and Gelatin for Drug Delivery," *Advanced Drug Delivery Review* 55: 1547-1567.

Ruszczak, Z. et al. (2003). "Collagen as a Carrer for On-site Delivery of Antibacterial Drugs," *Advanced Drug Delivery Review* 55: 1679-1698.

Sano, A. et al. (2003). "Atelocollagen for Protein and Gene Delivery," *Advanced Drug Delivery Review* 55: 1651-1677.

Toman, D. (2004). "Collagen Uses in Current and Developing Orthopaedic Therapies," *Methodologies Used in the Construction of Engineered Tissue* 33(5): 341-348.

Wallace, D. (2003). "Collagen Gel Systems for Sustained Delivery and Tissue Engineering," *Advanced Drug Delivery Review* 55: 1631-1649.

Butterfield, N. et al. (2001). "Combined pre-and post-surgical bupivacaine wound infiltrations decrease opioid requirements after knee ligament reconstruction," *Can. J. Anesth.* 48(3):245-250.

Finegold, H. (Date Unknown). "Applied Pharmacology of Local Anesthetics," located at <http://ramanathans.com/localchapter-ram[1].htm> visited on Jan. 20, 2005. (7 pages).

Geutjens, G. et al. (1994). "Analgesic effects of intraarticular bupivacaine after day-case arthroscopy," *Arthroscopy* 10:299-300.

Liguori, G. et al. (2002). "Possible bupivacaine toxicity after intraarticular injection for postarthroscopic analgesia of the knee: implications of the surgical procedure," *Anesth. Analg.* 94:1010-1013.

McGhan Medical Corporation. (2000). "Zyderm® Collagen Implant Physician Package Insert", 2 pages.

Purdue Pharm L.P. (1999). "Chirocaine® (Levobupivacaine Injection)" Catalog, 20 pages.

Spivey, W. et al. (1987). "A clinical comparison of lidocaine and bupivacaine," *Ann Emerg. Med.* 16:752-757.

Varrassi, G. et al. (1999). "Intra-articular buprenorphine after knee arthroscopy: a randomised, prospective, double-bind study," *Acta Annesthesiol. Scand.* 43:51-55.

Weiker, G. et al. (1991). "Serum lidocaine and bupivacaine levels in local technique knee arthroscopy," *Am. J. Sports. Med.* 19(5):499-502.

Batyrov, T.U. et al. (Mar.-Apr. 1982). "Experimental Study," *Stromatologiia* 61(2):7-10. (Certified English translation attached, 12 pages.)

Weiss, C. et al. (1987). "The Role of Na-hylan in Reducing Postsurgical Tendon Adhesions: Part 2," *Bull. Hosp. Jt. Dis. Orthop. Inst.* 47(1):31-39.

\* cited by examiner

Figure 1. *In vitro* bupivacaine release from collagen device over time.

Figure 2. Bupivacaine Release Rate

Figure 3. Percent Bupivacaine Retained in Sample

METHODS AND COMPOSITIONS FOR IMPROVED ARTICULAR SURGERY USING COLLAGEN

CROSS REFERENCE TO RELATED APPLICATIONS

This application claims the benefit of U.S. Provisional Patent Application Ser. No. 60/271,116, filed Feb. 23, 2001, the disclosure of which is incorporated herein by reference in its entirety.

TECHNICAL FIELD

The invention pertains to the field of joint injuries and damage, and surgical methods and compositions for treating such injuries and damage. The invention also pertains to the field of collagen, including the medical use of collagen formulations and the controlled release of pharmaceutical agents from collagen formulations.

BACKGROUND OF THE INVENTION

The joints of the skeletal system are the sites at which bones meet (articulate). In addition to bone, joints are formed by muscle, tendons and ligaments. Furthermore, protection of the joint is provided by cartilage and connective tissue, as well as by synovial fluid within the joint. When stressed, or as a result of the aging process, joints are prone to injury or degradation, leading to pain, impaired movement and decreased quality of life. Thus, approaches for repairing or treating damaged joints are highly desirable.

The earliest surgical approaches for joint repair involved cutting open the joint, referred to as open joint surgery or arthrotomy. However, because of the highly invasive nature of such procedures, the patient requires a hospital stay, often suffers severe and prolonged pain and faces a very long recovery time. In cases of extensive joint damage, surgical techniques have progressed such that reconstruction or replacement of the joint (arthroplasty) is an option. Again, however, these techniques are associated with considerable pain and recovery time for the patient.

The development of arthroscopic methods for articular surgery has greatly reduced the pain and recovery time experienced by patients as compared to arthrotomy. In arthroscopy, a small fiberoptic viewing instrument (the arthroscope), made up of a lens, light source and video camera, is inserted into the joint via a tiny (about ¼ of an inch) incision called a portal. Other portals are used for insertion of small (only 3 or 4 mm in diameter) surgical instruments. A video image is sent from the arthroscope to a television monitor, allowing the surgeon to have a clear view of the entire joint while operating. To maintain a clear field of view, the joint is continuously irrigated with an irrigation fluid during arthroscopic surgery. Various irrigation fluids have been tested, including water, 0.9% normal saline, Ringer's solution, 20% sorbitol, 2–10% mannitol and 1.5% glycine (Gradinger, R. et al. (1995) *Arthroscopy* 11:263–269; Mah E. T. et al. (1997) *Arthroscopy* 7:24–32). An irrigation fluid referred to as Synovisol, which is isomolar, nonhemolytic, nonantigenic, has a low viscosity and is nonconductive, has also been tested (Marshall, G. J. et al. (1988) *Arthroscopy* 4:187–193). A consequence of the need to continuously irrigate the joint during arthroscopy is that the normal synovial fluid is flushed from the joint.

The viscoelastic properties of synovial fluid are provided by the glycosaminoglycan molecule hyaluronan. Cross-linked forms of hyaluronan, referred to as hylans, have been used intra-articularly (for a review see e.g., Balazs, E. A. and Denlinger, J. L. (1989) *Ciba Found. Symp.* 143:265–275). For example, hylan fluid has been used as an irrigation fluid in arthroscopic surgery of the temporomandibular joint (McCain, J. P. et al. (1989) *J. Oral Maxillofac. Surg.* 47:1161–1168). Hyaluronic acid (HA-Hyalgan) and hylan G-F 20 (Synvisc) also have been used in the treatment of osteoarthritis (Frizziero, L et al. (1998) *Clin. Exp. Rheumatol.* 16:441–449; Marshall, K. W. et al. (2000) *J. Orthop. Res.* 18:416–425; Kroesen, S. et al. (2000) *Clin. Rheumatol.* 19:147–149). Use of hylan G-F 20 intra-articularly, however, has been reported in at least one case to induce an acute attack of calcium pyrophosphate dihydrate arthritis (Kroesen, S. et al. (2000) *Clin. Rheumatol.* 19:147–149). Na-hylan, a chemically modified sodium hyaluronate jelly, also has been used to reduce postsurgical tendon adhesions (Weiss, C. et al. (1986) *Bull. Hosp. Jt. Dis. Orthop. Inst.* 46:9–15; Weiss, C. (1987) *Bull. Hosp. Jt. Dis. Orthop. Inst.* 47:3139).

Arthroscopy has now become a common surgical procedure in current medical practice with almost 700,000 knee and shoulder arthroscopies performed each year in the United States. The post-operative course for these patients is marked by significant pain and resultant loss of limb function for the initial 3–5 days. Therapeutic intervention typically involves injection of a local anesthetic (e.g. bupivacaine) into the operated joint at the end of the procedure, resulting in pain relief for about 6 hours. It has been suggested that an intra-articular dose of approximately 10 mg produces analgesia of the joint (Creamer *J. Rheumatol.* (1996) 23:1031–1036). Thereafter, the patient is managed by administration of oral narcotics (e.g. Vicodin) and/or acetaminophen, and often neither of these results in sufficient pain relief. There exists a clinical need for a single dose product that can provide short term (2–5 days) post-arthroscopy pain relief.

Other surgical procedures are also often associated with significant pain, such as incisional pain. Such procedures include, most often, abdominal, breast and spinal operations, including cesarean births, hernia repair, hysterectomy, mastectomy, and breast augmentation. Other surgery involving pain or discomfort due to incision includes podiatry procedures.

An exogenous fibrin clot is another type of material that has been used in joint repair. An exogenous fibrin clot has been shown to promote fibrocartilaginous repair in an animal model of triangular fibrocartilage complex (TFCC) injury (Whately, J. S. et al. (2000) *Arthroscopy* 16:127–136). Furthermore, an exogenous fibrin clot has been used to enhance repair of an injured meniscus (Rodeo, S. A. and Warren, R. F. (1996) *Clin. Sports Med.* 15:469–481).

U.S. Pat. No. 3,949,073 by Daniels et al., U.S. Pat. No. 4,140,537 Luck et al., U.S. Pat. No. 4,424,208 by Wallace et al., U.S. Pat. No. 5,002,071 by Harrell, U.S. Pat. No. 4,760,131 by Sundsmo et al., EP 338813 by Tsunenaga et al. and U.S. Pat. No. 4,582,640 by Smestad et al. describe collagen formulations for use in soft tissue or connective tissue augmentation, for example reduction of skin wrinkles or scars. U.S. Pat. No. 4,764,377 by Goodson and U.S. Pat. No. 4,906,670 by Higashi et al. describe compositions containing collagen for the treatment of periodontal disease.

U.S. Pat. Nos. 6,083,918 and 6,165,983 by Klaus describes the use of collagen formulations for the treatment of degenerative arthrothopies while U.S. Pat. No. 3,966,908 by Balassa describes the use of cartilage powder for such treatments. Neither Klaus nor Balassa teach the use of particular types of collagen. Collagen from bovine skin sources, as used in Klaus, is generally Type I collagen, but, without further processing, would contain immunogenic telopeptide sequences (Rubin et al. (1965) *Biochemistry* 4(2):181–190). The collagen in cartilage powder is predominantly Type II collagen, which is frequently used to provoke immunogenic reactions in rats and other animals in order to model rheumatoid arthritis (Myers et al. (1997) *Life Sci.* 61(19):1861–1878; Brahn (1991) *Clin. Orthop.* 265:42–53). Steffen (1975) *A. Immun.-Forsch. Bd.* 150:432–446) examines the immunogenicity of soluble human collagen in rabbit knees. U.S. Pat. No. 4,704,273 by McMichael describes collagen containing formulations for the treatment of rheumatoid arthritis.

U.S. Pat. No. 5,639,796 by Lee et al. describes a composition comprising a hydrophilic polymer suspended in a hydrophobic carrier and its use for replacing natural lubricating fluids of the body.

U.S. Pat. No. 4,703,108 by Silver et al. describes the production of biodegradable matrices using crosslinked collagen.

Despite advances in articular surgical methods, there still exists a need for approaches that are effective in diminishing patient pain, increasing joint mobility post-surgery and/or reducing recovery time and that are generally applicable to the various articular surgery options (e.g., arthrotomy, arthroscopy, arthroplasty) or other surgical procedures associated with incisional pain. When providing extended treatment of pain or discomfort, as through the controlled release of pharmaceutical agents, it is essential that the compositions or devices employed for the controlled release of substances are non-immunogenic and well tolerated by the patient (Cooperman et al. (1984) *J. Am. Acad. Dermatol.* 10:638–646; DeLustro et al. (1988) *Dermatol. Surg. Oncol.* 14:57–65; DeLustro et al. (1987) *Plast. Reconstruct. Surg.* 79:581–592; Frank et al. (1991) *Plast. Reconstruct. Surg* 87:1080–1088).

Citation of the references above is not an admission that these references, or the information disclosed therein, is prior art.

SUMMARY OF THE INVENTION

This invention provides improved surgical methods and controlled release formulations for treating an articular injury of a joint in a patient, in which a collagen formulation is used in conjunction with a surgical procedure to treat the articular injury. Collagen formulations of the invention and their use, in addition to the surgical procedure, may provide at least one or more of the following benefits: reduced patient pain, shortened recovery time and/or improved joint condition (e.g., treatment of the underlying articular injury). Moreover, the methods and compositions of the invention can be used in conjunction with essentially any surgical procedure used to treat an articular injury. The invention further provides compositions and methods for treating post-surgical articular or incisional pain or discomfort in a patient.

In one embodiment, a composition for the treatment of post-surgical pain or discomfort in a joint or along an incision according to the invention consists essentially of an aqueous dispersion of insoluble non-crosslinked type I fibrillar atelopeptide collagen and a pharmaceutical agent, wherein the composition is formulated to release an effective amount of the pharmaceutical agent from the collagen for at least 48 hours.

In particular embodiments the pharmaceutical agent may be selected from the group consisting of anesthetics, analgesics, antibiotics, sedatives, opioids and antitumor agents.

A method of the invention includes a method for the treatment of post-surgical pain or discomfort in a joint(s) comprising the step of intra-articularly administering to a joint(s) in a patient a composition consisting essentially of an aqueous dispersion of insoluble non-crosslinked type I fibrillar atelopeptide collagen and a pharmaceutical agent, where the composition is formulated to release an effective amount of the pharmaceutical agent from the collagen for at least 48 hours. The composition may be administered before, during or after a surgical procedure, including immediately after the surgical procedure. The pharmaceutical agent may be, for example, an analgesic, antibiotic, anesthetic, sedative, opioid or antitumor agent.

In another embodiment, the invention includes a composition for the treatment of post-surgical articular or incisional pain or discomfort consisting essentially of an aqueous dispersion of insoluble non-crosslinked type I fibrillar atelopeptide collagen and bupivacaine; wherein the composition is formulated to release an effective amount of bupivacaine from the collagen for at least 48 hours.

An additional method of the invention includes a method for the treatment of post-surgical pain or discomfort in a joint(s) comprising the step of intra-articularly administering to a joint(s) in a patient a composition consisting essentially of an aqueous dispersion of insoluble non-crosslinked type I fibrillar atelopeptide collagen and bupivacaine, where the composition is formulated to release an effective amount of bupivacaine from the collagen for at least 48 hours.

In another embodiment, the invention is directed to a method for the treatment of post-surgical pain or discomfort associated with one or more incisions comprising the step of administering to a patient's incision(s) a composition as described herein, where the composition is administered before, during or after a surgical procedure. The incision(s) may be associated with a surgical procedure such as, but not limited to, abdominal surgery, such as a cesarean birth, hysterectomy, hernia repair; breast surgery, such as a breast augmentation or mastectomy; spinal operations, or podiatry procedures. The composition may be administered in a premeasured amount.

In another embodiment, the invention is directed to a method for the treatment of post-surgical pain or discomfort associated with one or more incisions comprising the step of administering to a patient's incision(s) a composition consisting essentially of an aqueous dispersion of insoluble non-crosslinked type I fibrillar atelopeptide collagen and bupivacaine, where the composition is administered before, during or after a surgical procedure. The incision(s) may be associated with a surgical procedure such as, but not limited to, abdominal surgery, such as a cesarean birth, hysterectomy, hernia repair; breast surgery, such as a breast augmentation or mastectomy; spinal operations, or podiatry procedures. The composition may be administered in a premeasured amount.

The methods of the invention may also comprise: performing a surgical procedure on the joint; and administering to the joint a composition comprising an aqueous dispersion of insoluble collagen in a sufficient premeasured amount such that it effectively reduces patient pain, increases joint mobility post-surgery and/or reduces recovery time.

In some embodiments the composition consists essentially of 3–100 mg/ml collagen. In certain embodiments, the composition consists essentially of about 5–10 mg/ml collagen, about 10–100 mg/ml collagen or about 20–100 mg/ml collagen, in others about 65 mg/ml collagen. The source of the collagen can be, for example, bovine skin. Alternatively, human collagen can be used. Typically, the collagen of the composition is predominantly non-crosslinked, insoluble, atelopeptide fibrillar Type I collagen. In some embodiments the collagen is at least 95% non-crosslinked, atelopeptide insoluble, fibrillar Type I collagen.

In one embodiment, the composition further consists essentially of at least one additional pharmaceutical agent. Examples of suitable additional pharmaceutical agents include anesthetics, analgesics, antibiotics, opioids, sedatives and antitumor agents. The pharmaceutical agent may include lidocaine, bupivacaine or morphine at concentrations up to 20 to 30 mg/ml. Pharmaceutical agents as described herein may be used in concentrations up to about 20 to 30 mg/ml. In particular embodiments the concentration can be up to about 30 mg/ml, up to about 20 mg/ml, up to about 10 mg/ml or up to about 5 mg/ml. The concentration of the pharmaceutical agent in other embodiments may be about 4–30 mg/ml, about 4–20 mg/ml, about 4–15 mg/ml, about 10 mg/ml or about 5 mg/ml. In certain embodiments the concentration of pharmaceutical agent is greater than 3 mg/ml, greater than 4 mg/ml or greater than 5 mg/ml.

In particular embodiments the pharmaceutical agent may be selected from the group consisting of anesthetics, analgesics, antibiotics, sedatives, opioids and antitumor agents. Particular examples of anesthetics/analgesics include, but are not limited to bupivacaine, lidocaine, procaine, tetracaine, mepivacaine, etidocaine or procainamide. Particular classes of antibiotics for use as pharmaceutical agents include, for example, but are not limited to, tetracyclines, cephalosporins, chloramphenicols, and aminoglycosides (e.g. amikacin, gentamicin). Examples of opioids include, but are not limited to morphine, codeine, demerol, or methadone and examples of sedatives may include diazepam or flurazepam. Antitumor agents may also be used as the pharmaceutical agent and may include, but are not limited to methotrexate or tamoxifen.

In a preferred embodiment, the composition is an injectable insoluble aqueous solution of Type I fibrillar collagen from bovine skin that contains an analgesic/anesthetic agent such as lidocaine, bupivacaine or morphine at concentrations up to about 20 to 30 mg/ml.

In certain embodiments, the total amount of pharmaceutical agent released from the composition is from about 5 mg to about 1 g. In other embodiments, the amount of pharmaceutical agent released is about 2 mg to about 15 mg per day or about 10 mg per day.

In some embodiments, the ratio of collagen to pharmaceutical agent can be about 0.5:1 to about 50:1 or about 1:1 to about 5:1. In particular embodiments the ratio of collagen to pharmaceutical agent is about 1:1.

The methods of the invention can be used with a variety of surgical procedures, including arthroscopy, arthrotomy, implantation of chondrocytes, implantation of cartilage, total joint arthroplasty or partial joint arthroplasty or non-articular surgical procedures including abdominal, breast, spinal or podiatry procedures. Chondrocytes and cartilage implants may be allografts, autografts or xenografts. The methods of the invention can be used for the treatment of essentially any joint upon which surgery is performed. A preferred joint is the knee. Other suitable joints include, but are not limited to, shoulders, ankles, hips, wrists, elbows and temporomandibular joints.

The methods of the invention can be used in the treatment of a wide variety of articular injuries. Nonlimiting examples include: meniscal injury, anterior cruciate ligament injury, rotator cuff injury, carpal tunnel syndrome, synovitis, chondromalacia, patellar tendon rupture, tibial tubercle fracture, loose bodies of bone or cartilage, osteochondritis dissecans, adhesive capsulitis, impingement syndrome, shoulder dislocation, Dupuytren's syndrome, scaphoid fracture, stenosing tenosynovitis, lateral facet syndrome, anterior patellofemoral pain syndrome, lateral pressure syndrome, malalignment syndrome, maltracking syndrome and degenerative articular processes, such as osteoarthritis. In one embodiment of the invention, the articular injury does not result from a degenerative articular process.

The collagen compositions described herein can be administered into the joint by any means that results in the collagen composition being inserted intraarticularly, but preferably is administered via a catheter. The composition preferably is administered intraarticularly during the surgical procedure, e.g., prior to closure of the incision(s), but alternatively can be administered before or following the surgical procedure (e.g., by intraarticular injection following surgery). The composition may be delivered via a cannula.

The methods of the invention can be carried out on patients in need of treatment for articular injuries, including human patients and veterinary patients, such as horses and dogs.

Another aspect of the invention pertains to a catheter for treating an articular injury of a joint in a patient. The catheters of the invention comprise a lumen and are adapted for use in arthroscopy or arthrotomy. Furthermore, the catheter comprises in its lumen a composition as described herein in a premeasured amount sufficient to treat an articular injury of a joint in a patient. Preferably, the composition consists essentially of about 3–100 mg/ml collagen, more preferably about 65 mg/ml collagen. The source of the collagen can be, for example, bovine skin. Alternatively, human collagen can be used. Typically, the collagen of the composition is predominantly Type I collagen. In certain embodiments the collagen is at least 95% insoluble fibrillar non-crosslinked atelopeptide Type I collagen. In one embodiment, the composition further consists essentially of at least one additional pharmaceutical agent. Examples of suitable additional pharmaceutical agents include anesthetics, analgesics, antibiotics, anti-inflammatory agents, growth factors, lubricating agents, antitumor agents, sedatives, opioids, collagenase inhibitors.

DETAILED DESCRIPTION OF THE INVENTION

The invention described herein pertains to formulations of aqueous dispersions of insoluble, fibrillar, non-crosslinked, atelopeptide Type I collagen and at least one pharmaceutical agent which are capable of providing the controlled release of the pharmaceutical agent over time. This invention also pertains to methods for using such formulations to treat pain and/or discomfort accompanying surgical procedures associated with the treatment of articular injuries as well as the pain and/or discomfort associated with surgical incisions or the pain of the injuries themselves. These formulations offer distinct advantages in the management and treatment of post-surgical pain and discomfort in that they provide a means of managing pain for a period of about 2–5 days post-surgery without the administration of a large, immediately-released and limited-duration bolus of pharmaceutical agent, for example, an analgesic, and diminish or eliminate the need for additional pain management, such as over-the-counter analgesics, or prescription drugs, such as narcotics.

Throughout this disclosure, various publications, patents and published patent applications are referenced by an identifying citation. The disclosures of these publications, patents and published patent applications are hereby incorporated by reference into the present disclosure to more fully describe the state of the art to which this invention pertains.

As used herein, the term "articular injury" is intended to encompass damage to a joint (i.e., a change from the normal architecture or function of the joint), whether as a result of stress, overuse, a sports or other accident, disease, infection or aging.

As used herein, the term "treating", and its cognates such as "treatment", is intended to refer to ameliorating or alleviating one or more symptoms of the articular injury or the condition for which the patient is being treated or the pain or discomfort associated with the injury or the treatment of such injury, as in a surgical procedure. The term "treating" is also intended to encompass the use of the compositions and methods described herein in the amelioration or alleviation of the pain or discomfort associated with incisions resulting from surgery. Treatment of infection, which may be an underlying cause of the articular injury, or may be a possible complication of the surgical procedure, is also contemplated. For example, antibiotics or other pharmaceutical agents may be used to treat the infection and further may be used prophylactically to prevent infection from developing. Such treatment may also result in reduced inflammation or pain associated with infection due to the treatment or amelioration of the infection.

As used herein, the term "joint" is intended to encompass any joint of the skeletal system, including but not limited to knees, shoulders, ankles, hips, wrists, elbows and temporomandibular joints.

As used herein, the term "patient" is intended to encompass vertebrates that may be in need of treatment for articular injuries or the pain or discomfort resulting from surgical procedures. Preferred subjects are mammals. Even more preferred subjects are humans and veterinary patients, including farm animals, sport animals, and pets, such as horses, dogs, cats, cows, sheep and goats.

As used herein, the term "surgical procedure" is intended to encompass any technique in which the internal architecture of the joint is manipulated by inserting at least one instrument into the joint. Examples include arthrotomy, arthroscopy and arthroplasty (total or partial). "Surgical procedure" is also intended to include abdominal, breast, podiatry and spinal operations, including cesarean births or deliveries (i.e. a "C-section"). The terms "surgical procedure", "operation" and "surgical operation" can be used interchangeably herein.

As used herein, the term "administer" is intended to encompass introduction of a composition into a joint or along an incision, by whatever means, including but not limited to: via a catheter or cannula or via injection.

As used herein, the term "pharmaceutical agent" is intended to encompass compounds having pharmaceutical activity, nonlimiting examples of which include anesthetics, analgesics, sedatives, opioids, antitumor agents, antibiotics, anti-inflammatory agents, growth factors, polynucleotides, proteins, polypeptides, peptides, chemotherapeutic agents and the like.

As used herein, the term "therapeutically effective amount" or "effective amount" is intended to refer to an amount (e.g., of a pharmaceutical agent) sufficient to achieve treatment of an articular injury or incisional pain (including discomfort) being treated or amelioration of the symptoms of the injury or of the treatment (e.g., pain associated with a surgical procedure).

As used herein, the term "degenerative articular process" is intended to refer to an articular injury.

As used herein, the term "dispersion" refers to a liquid suspension of insoluble material in which the insoluble solid material cannot be separated from the liquid portion of the dispersion by centrifugation (e.g. the solid cannot be formed into a pellet by centrifugation). This is distinguished from suspensions of insoluble material which can be separated and/or formed into a pellet by centrifugation.

"Type I" collagen refers to the major collagen present in tendon and bone. Other sources of Type I collagen include skin, lung, dentin, heart valese, fascia, scar tissue, cornea, and liver.

"Type II" collagen is the predominant collagen in cartilage, while "Type III" collagen can be found in dermal sources of collagen.

As used herein the term "atelopeptide" refers to the collagen in which the "telopeptide" sequences have been removed. The term "telopeptide" refer to the non-helical terminal regions of collagen. These telopeptide regions are believed to be largely responsible for the immunogenicity of xenogenic collagen (Rubin et al., (1965) *Biochemistry* 4(2): 181–190). "Telopeptide collagen" refers to collagen with these sequences intact. The telopeptide sequences of Type I collagen contains tyrosine, while the helical regions of Type I collagen do not. Atelopeptide collagen versus telopeptide collagen can be distinguished based on amino acid analysis, in which atelopeptide collage should contain less than about 1.5 tyrosine residues per 1000 amino acids, while telopeptide collagen contains approximately 3–4 tyrosine residues per 1000 amino acids. Treatment with the enzyme pepsin is one method for removing the telopeptide sequences from collagen.

Collagen can exist in non-fibrillar or fibrillar form. Non-fibrillar collagen consists of triple helices which are approximately 300 nm long and 1.5 nm in diameter (Piez K, "Collagen", in *Encyclopedia of Polymer Science and Engineering, vol.* 3, pages 699–727, 2nd Ed., John Wiley (1985)). In comparison, fibrillar collagen may exist in a wide array of fibrillar sizes ranging from diameters of about 3–30 nm up to about 1000 nm, with the fibral length ranging from 400–500 nm to up to about 5000 nm. The smallest fibrils arise when 5 to about 30 triple-helical molecules associate. (Gelman, et al.(1979) *J. Biol. Chem.* 254:11741–11745; Capaldi, et al. (1982) *Biopolymers* 21:2291–2313). Collagen fibril size can readily be determined using differential scanning calorimetry (DSC) to measure melting temperatures. In general, non-fibrillar collagen melts at 39–40° C., whereas microfibrillar collagen melts at 42–46° C. See, for example, Wallace, et al. (1986) *Biopolymers* 25:1875–1893.

As used herein, the term "non-crosslinked" refers to collagen molecules which do not have synthetic chemical bonds between the alpha chains of the fibril. Thus, for example, fibrillar collagen may be crosslinked or non-crosslinked depending on the presence of such attachments.

Additional discussion regarding types of collagen may be found in Piez K, "Collagen", in *Encyclopedia of Polymer Science and Engineering*, vol. 3, pages 699–727, 2nd Ed., John Wiley (1985).

The invention provides methods that are effective in diminishing patient pain, increasing joint mobility post-surgery and/or reducing recovery time.

One method of the invention comprises: performing a surgical procedure on the joint; and administering to the joint a composition comprising an aqueous dispersion of insoluble collagen, in a sufficient premeasured amount such that it effectively reduces patient pain, increases joint mobility post-surgery and/or reduces recovery time.

An additional method of the invention includes a method for the treatment of post-surgical pain or discomfort in a joint(s) comprising the step of intra-articularly administering to a joint(s) in a patient a composition containing an aqueous dispersion of insoluble non-crosslinked type I fibrillar atelopeptide collagen and a pharmaceutical agent, where the composition is formulated to release an effective amount of the pharmaceutical agent from the collagen for at least 48 hours. The composition may be administered before, during or after a surgical procedure, including immediately before or after the surgical procedure. The additional pharmaceutical agent may be, for example, an anesthetic, analgesic, antibiotic, sedative, opioid or antitumor agent.

The methods of the invention further include method for the treatment of post-surgical pain or discomfort associated with one or more incisions comprising the step of administering to a patient's incision(s) a composition as described herein, wherein the composition is administered before, during or after a surgical procedure.

In certain embodiments the incision is associated with surgical procedures including abdominal surgery (e.g. a cesarean birth, hernia repair, hysterectomy), spinal surgery or other surgery involving pain or discomfort due to incision (e.g. mastectomy, breast augmentation, podiatry procedures). The compositions as described herein may be administered to one or more locations along the incision in conjunction with the method of the invention. In certain embodiments administration to an incision(s) is via injection. The compositions as described herein are of particular use in that they may be administered through a 32 or larger diameter gauge needles. In certain embodiments the compositions may be administered via 20 gauge needles. The ability to administer these compositions with needles of such diameter eliminates or reduces the need for the use of topical or other anesthetics or analgesics.

The collagen compositions used in the methods of the invention can be prepared using methods known in the art. The composition may contain of about 3–100 mg/ml collagen. In certain embodiments the concentration of collagen is about 10–100 mg/ml collagen, about 20–100 mg/ml collagen, about 20–50 mg/ml, about 16 mg/ml–28 mg/ml. The composition may comprise collagen including collagen from bovine skin (dermal), human collagen or Type I collagen. In particular embodiments the collagen is insoluble non-crosslinked Type I fibrillar atelopeptide collagen. In certain embodiments the collagen is at least 95% insoluble fibrillar non-crosslinked atelopeptide Type I collagen. In some embodiments the collagen contains less than 5% Type III collagen. The collagen may be prepared as an aqueous dispersion of insoluble non-crosslinked type I fibrillar atelopeptide collagen.

The composition may further contain at least one additional pharmaceutical agent. The pharmaceutical agent may be selected from the group consisting of: anesthetics, analgesics, antibiotics, sedatives, opioids and antitumor agents.

In certain embodiments, the composition may further contain a pharmaceutically acceptable excipient. Such excipients are well known to those of skill in the art and include, but are not limited to, pharmaceutically acceptable buffers, emulsifiers, polyethylene glycol (PEG), and saccharides (e.g. mannitol).

The methods of the invention may also comprise performing arthroscopy; arthrotomy (total or partial), implantation of cartilage or implantation of chondrocytes. Cartilage and chondrocytes for implantation may be allografts, autografts or xenografts.

In the methods of the invention, the joint may be a knee, a shoulder, an ankle, a hip, a wrist, an elbow or a temporomandibular joint.

In the methods of the invention, the articular injury may result from conditions including, a meniscal injury; an anterior cruciate ligament injury rotator cuff injury, carpal tunnel syndrome, synovitis, chondromalacia, patellar tendon rupture, tibial tubercle fracture, loose bodies of bone or cartilage, osteochondritis dissecans, adhesive capsulitis, impingement syndrome, shoulder dislocation, Dupuytren's syndrome, scaphoid fracture, stenosing tenosynovitis, lateral facet syndrome, anterior patello-femoral pain syndrome, lateral pressure syndrome, malalignment syndrome and maltracking syndrome.

In the methods of the invention, the articular injury does not necessarily result from a degenerative articular process.

In the methods of the invention, the composition may be administered intraarticularly via a catheter, cannula or injected.

In the methods of the invention, the composition may be administered intraarticularly or along an incision(s), before, during or following the surgical procedure. In particular embodiments for the treatment of incisional pain, the composition is administered before the surgical procedure, that is, before an incision is made, in the vicinity of the expected incision. In certain embodiments, the methods of the invention as described herein may further comprise the step of at least one additional administration of a composition as described herein. In certain embodiments, the additional administration may occur immediately after the surgical procedure, as when the composition is administered before the procedure. In other embodiments the additional administration may occur during the procedure or after the procedure, for example, 1 minute after, 2 minutes after, 5 minutes after, 10 minutes after, 15 minutes after, 25 minutes after, 30 minutes after, 45 minutes after, 1 hour after, 2 hours after, 3 hours after, 6 hours after, 8 hours after, 9 hours after, 12 hours after or 18 hours after the surgical procedure. In certain embodiments, the additional administration may occur about 2, 3, 4, 5 or 6 days after the initial administration and surgical procedure to treat continued pain or discomfort. In particular embodiments the additional administration can be administered via injection.

In the methods of the invention, the patient may be a human patient or a veterinary patient.

The present invention is also directed to a catheter for treating an articular injury of a joint in a patient, the catheter comprising a lumen and being adapted for use in arthroscopy or arthrotomy, wherein the catheter comprises in its lumen a composition as described herein in a sufficient premeasured amount such that it effectively reduces patient pain, increases joint mobility post-surgery and/or reduces recovery time.

The compositions of the invention, including those incorporated into the catheter described herein may contain about 3–100 mg/ml collagen. In another embodiment the composition may contain about 10–100 mg/ml collagen, about 20–100 mg/ml collagen, about 20–50 mg/ml collagen, about 15–100 mg/ml collagen, or about 16–28 mg/ml collagen. The collagen may be from bovine skin, may be human collagen and is predominantly insoluble, non-crosslinked, fibrillar, atelopeptide Type I collagen. In certain embodiments the collagen is at least 95% insoluble, non-crosslinked, fibrillar, atelopeptide Type I collagen. In some embodiments the collagen contains less than 5% Type III collagen. The collagen may be prepared as an aqueous dispersion of insoluble non-crosslinked type I fibrillar atelopeptide collagen for combination with the pharmaceutical agent.

The insoluble non-crosslinked type I fibrillar atelopeptide collagen as used herein is prepared using the following steps. The hide is cleaned, solubilized with acid, filtered, then enzymatically treated to remove the telopeptides. This results in a clear collagen dispersion of solubilized collagen fibers at low pH. This resulting product is further clarified and treated to eliminate virus and/or prion particles. Then through a series of steps known to those of skill in the art using bases and salt, the protein is precipitated and concentrated (for example, to 120 mg/mL collagen) then diluted again to make the dispersion of the desired concentration of insoluble non-crosslinked, fibrillar, atelopeptide Type I collagen used herein. Preparation of collagen is further described in U.S. Pat. Nos. 4,233,360, 5,616,689 and 4,140,537 and Piez K, "Collagen", in *Encyclopedia of Polymer Science and Engineering, vol.* 2, 2nd edition, 1985.

The compositions may further include at least one additional pharmaceutical agent. The pharmaceutical agent may be selected from anesthetics, analgesics, antibiotics, sedatives, opioids and antitumor agents. In particular embodiments the pharmaceutical agent is in solution (i.e. is solubilized at a given concentration) when combined with the collagen.

Compositions and devices for the controlled release of pharmaceutical reagents within joints are limited by the residence time the composition spends in the joint itself, and can therefor serve to deliver the agent. Synovial fluid is renewed continuously, with estimates from 0.5 hours to 48 hours for complete renewal of the synovial fluid (Altman (1992) *Laboratory Findings in Osteoarthritis* Chapter 12, pg. 316 in *Osteoarthritis, Diagnosis and Medical/Surgical Management*, Moskowitz, Howell, Goldberg and Mankin, Eds., WB Saunders, Philadelphia, Pa.). The compositions or carriers for the controlled release devices are usually cleared or removed from the joint within about 24 hours. One example of this is viscosupplement hyaluronic acid. Its use as a drug delivery matrix is limited by its rapid clearance from the joint (Fraser et al. (1993) *Sem. Arthritis and Rheumatism* 22(6) Suppl. 1:9–17).

Results show that collagen similar to that described herein has been observed to remain in the knee joints in animals for up to 8 weeks. Fibrillar, highly purified Type I collagen has previously been shown to be safe for in vivo use (Pavelka et al. (June 1999) Poster No. 001096 *XIV European League Against Rheumatism Congress*, Glasgow, Scotland and (June 1999) 4*th Congress of the European Federation of National Associations of Orthapaedics and Traumatology*, Brussels, Belgium; Pavelka et al. (September 1999) *Fourth World Congress of the OsteoArthritis Research Society International*, Vienna, Austria). ZYDERM, a formulation of insoluble non-crosslinked fibrillar atelopeptide collagen Type I and 0.3% (3 mg/mL) lidocaine is commercially available (Inamed Anesthetics, Santa Barbara, Calif.) and used primarily for collagen replacement under the skin. As described in Pavelka (supra), 1 mL intra-articular injections of formulations of collagen have been used in the treatment of osteoarthritis. However, results show that the amount of lidocaine present in these injections is not effective for pain management over time, with the anesthetic effects of lidocaine lasting less than an hour, in most cases only a few minutes (e.g. less than 10 minutes). Collagen has also been used in a matrix for the controlled delivery of protein growth factors (Shroeder-Teft et al. (1997) *Controlled Release* 49:291–298; Bentz et al. (1998)*J. Biomed. Mater. Res.* 39:539–548; McPherson et al. (1988) *Coll. Relat. Res.* 8(1):65–828:65–82; Rosenblatt et al. (1989) *J. Controlled Release* 9:195–203.

While not wishing to be bound by theory, it is postulated that the insoluble non-crosslinked, fibrillar atelopeptide Type I collagen used in the present invention promotes the slow release of the pharmaceutical agent through a binding interaction between the collagen and the pharmaceutical agent. Lidocaine and related pharmaceutical agents are known to bind to collagen or possess characteristics that allow the development of compositions for drug delivery over time (Shroeder-Teft et al. (1997) supra; Bentz et al. (1998) supra). Such characteristics include a lipophilic aromatic group, a connector and a hydrophilic amine group. A number of other classes of pharmaceutical agents which contain an aromatic group and a charged or highly polar group and which also may bind collagen include, but are not limited to anti-arrhythmic drugs (e.g. disopyramide); analgesic/anesthetic drugs (e.g. procaine, procainamide, lidocaine, bupivacaine, tetracaine, mepivacaine, etidocaine); adrenergic receptor blocking drugs (e.g. dolbutamine); sympathomimetic drugs (e.g. epinephrine, ephedrine, amphetamine, dopamine); antimuscarinic agents (e.g. scopolamine, atropine); cholinesterase inhibitors (e.g. neostigmine, physostigmine); antidepressants (e.g. imipramine); sedatives (e.g. diazepam (Valium), flurazepam); anti-inflammatories (e.g. indomethacin); opioids (e.g. morphine, codeine, methadone, demerol); diuretics (e.g. amiloride, triamterene); anti-estrogens (e.g. clomiphene); anti-histamines (e.g. chlorpheniramine, cimetidine, triprolidine); serotonin antagonists and serotonin-like drugs (e.g. N,N dimethyl tryptamine, psilocybin); sulfonamides (e.g. sulfadiazine, sulfamerazine); anti-malarials (e.g. chloroquine); anti-helmintics (e.g. bephenium hydroxy-naphthoate; anti-tumor drugs (e.g. methotrexate, tamoxifen) and antibiotics (e.g. classes including: tetracyclines, cephalosporins, chloramphenicols, and aminoglycosides (e.g. amikacin, gentamicin)). Other antibiotics known in the art may also be used as pharmaceutical agents, including those disclosed in U.S. Pat. App. Nos. 20020004499, 20010049366 and U.S. Pat. Nos. 6,316,033, 6,322,592, 6,087,355 and 6,316,015. Another class of pharmaceutical agents which are known to bind to collagen are the anti-coagulants (e.g. heparin) (McPherson et al. (1988) *Coll. Relat. Res.* 8(1):65–828:65–82).

The current standard of care in the United States is to inject a large bolus (≈20–30 mL) of anesthetic/analgesic into the joint and discharge the patient with a prescription for low-strength oral narcotics (e.g. Vicodin). The local anesthetic is typically a cocktail of lidocaine, bupivacaine, and/or morphine (Cepeda et al., (1997) *Reg. Anesth.* 22:223–238) and its duration of effectiveness is approximately 6 hours. The patients experience pain for three to five days and require extensive management with narcotics and cryotherapy, tapering to non-steroidal anti-inflammatory drugs (NSAIDs) and/or acetaminophen plus cryotherapy thereafter.

Bupivacaine is an amide-type local anesthetic/analgesic, chemical related to lidocaine. However, lidocaine requires 2 to 10 times the dosage to achieve the same clinical efficacy for equivalent indications (Cepeda et al., supra). Creamer (*J. Rheumatol.* (1996) 23:1031–1036) reported a statistically significant (p=0.007) fall in VAS pain scores at 1 hour post-intra-articular administration of 12.5 mg bupivacaine in the knees of osteoarthritis patients, but no significant effects were seen after 1 hour. Others describe the use of a single intra-articular bolus administration, either pre- or postoperatively, of 50 to 150 mg of bupivacaine for postoperative analgesia following arthroscopic knee surgery (Kaeding et al. (1990) *Arthroscopy* 6:33–39; Wasudev et al. (1990) *Arthroscopy* 6:40–42; Solanki et al. (1992)*Arthroscopy* 8:44–47; Smith et al. (1991) *Anesth. Analg.* 73:536–539; Henderson et al. (1990) *Am. J. Sports Med.* 18:614–617). The duration of analgesia from an intra-injection of bupivacaine is generally reported to be 2 to 12 hours (Cepeda supra; DeAndres et al. (1998) *Eur. J. Anaesth.* 15:10–15; Debruyne et al. (1985) *Eur. J. Clin. Pharmacol.* 27:733–735; Meinig et al. (1988) *Am. J. Sports Med.* 16(3):295–300).

As would be understood by one of skill in the art, the compositions recited herein may be formulated to vary the amount of pharmaceutical agent released and/or the amount of time over which an effective amount of the agent is released by varying the concentration of the pharmaceutical agent and/or the collagen. For example, a greater duration of controlled release (longer time period over which the agent is released at an effective amount) could be achieved by increasing the concentration of collagen, relative to the concentration of pharmaceutical agent. Concomitantly the ratio of collagen to agent will increase. The duration of post-surgical pain treatment may also be increased by administering a greater amount of the compositions of the invention such that a greater amount of the pharmaceutical agent (as present in the composition) is present within the joint(s) or incision(s) of the patient.

In certain embodiments, the amount of the compositions, as described herein, which are administered can be greater than 1 mL. In other embodiments the amount of composition administered is greater than 2 mL, greater than 3 mL, greater than 4 ml, greater than 5 mL, greater than 10 mL, or greater than 20 mL. In particular embodiments the amount of composition administered may be, for example, but not limited to about 2 mL, about 5 mL, about 10 mL, about 15 mL, about 20 mL, about 25 mL, about 30 mL, about 35 mL or about 40 mL. One of skill in the art would know to adjust the amount of the composition administered, and therefore the amount of pharmaceutical agent delivered, depending on the type of surgical procedure performed (e.g. cesarean birth, arthroscopy, joint replacement, mastectomy, hernia repair, hysterectomy, podiatry, breast augmentation, etc.), the site of the procedure (e.g. knee, abdomen, spine, breast, foot, etc.) and the severity or duration of pain or discomfort likely or usually associated with the procedure performed, as well as the pain tolerance of the patient and the particular composition being administered. These criteria will also be considered by the skilled practitioner when determining whether additional administrations of the compositions should or will be administered.

As will also be appreciated by one of skill in the art, the formulation of the composition will also be tailored for the particular pharmaceutical agent which is being delivered, taking into account the effective amount of pharmaceutical agent to be released such that the amount released at a given time, or throughout the duration of delivery, is not toxic to the patient. Information regarding the toxicity and half-life of known pharmaceutical agents is readily available. For example, bupivacaine is known to have a half life in adults of approximately 3.5 hours. A similar compound (levobupivacaine) has been shown to be non-genotoxic by standard mutagenicity and clastogenicity assays (Summary of Product Characteristics for CHIROCAINE, levobupivacaine for injection). Therapeutic apparently safe doses of bupivacaine are approximately 225 mg as a single bolus. The maximum dose of bupivacaine is 400 mg over a 24 hour period, and a single dose of 4.4 mg/kg (≈350 mg in an adult human) produced seizures in research monkeys, while the intravenous and subcutaneous $LD_{50}$ in mice is 6 to 8 mg/kg and 38 to 54 mg/kg respectively (Physicians Desk Reference, Medical Economic Company, Montvale N.J., $53^{rd}$ edition).

In certain embodiments, the total amount of pharmaceutical agent released from the composition is from about 5 mg to about 1 g, about 10 mg to about 1 g, about 15 mg to about 1 g. In certain embodiments the total amount of pharmaceutical agent released is about 0.25 g, about 0.5 g, about 0.75 g, about 1.0 g, about 1.25 g or about 1.5 g. In other embodiments the total amount of pharmaceutical agent released from the composition is from about 10 mg to about 500 mg, from about 10 mg to about 250 mg, from about 10 mg to about 125 mg, from about 10 mg to about 50 mg. In other embodiments, the amount of pharmaceutical agent released is about 2 mg to about 15 mg per day, about 5 mg to about 15 mg per day, about 7 mg to about 15 mg per day, about 10 mg to about 15 mg per day. In other embodiments, the amount of pharmaceutical agent released is about 5 mg per day or about 10 mg per day.

In some embodiments, the ratio of collagen to pharmaceutical agent can be about 0.5:1 to about 50:1, about 0.5:1 to about 40:1, about 0.5:1 to about 25:1, about 0.5:1 to about 15:1, about 0.5:1 to about 10:1, about 1:1 to about 5:1, about 1:1 to about 4.7:1, or about 3:1 to about 5:1. In particular embodiments the ratio of collagen to pharmaceutical agent is about 1:1.

In some embodiments the composition is formulated to release an effective amount of pharmaceutical agent for at least about at least about 50 hours, at least about 60 hours, at least about 72 hours, at least about 84 hours, at least about 96 hours, at least about 108 hours, at least about 120 hours. In certain embodiments, the composition is formulated to release an effective amount of pharmaceutical agent for about 2–5 days, about 2–3 days or about 2–4 days.

Any of the compositions as described herein may be used in conjunction with any of the methods of the invention. The catheter of the present invention may incorporate any of the compositions as described herein and may be used, as appropriate, in conjunction with any of the methods as described herein.

The invention will be better understood by reference to the following non-limiting examples.

EXAMPLES

Example 1

Formulations of Collagen and Bupivacaine for Controlled Release

The formulations described below were prepared using the following common procedures. A collagen gel ((65 mg/ml dispersion of Type I, bovine non-crosslinked fibrillar atelopeptide collagen in phosphate buffered saline) available from McGhan Medical (Santa Barbara, Calif.)) was syringe-to-syringe mixed with bupivacaine (0.75% bupivacaine HCL, Inj. USP, 7.5 mg/ML; Abbott Laboratories (North Chicago, Ill.)) (BU) solution, then incubated overnight at room temperature. The sample was transferred into cellulose dialysis tubing (Spectra/Por 1 Dialysis Membrane, 6000–8000 cut off, Spectrum Labs, Rancho Dominguez, Calif.) and the mass of the sample (i.e. the collagen+bupivacaine+dialysis tubing) was recorded. The sample was placed into 30 mL of phosphate buffered saline (50 mM sodium phosphate, 130 mM sodium chloride, pH 7.1) (PBS) at 34° C. At various timepoints up to 72 hours, the amount of BU in the PBS was measured by a spectrophotometer. After each timepoint, the sample was transferred to 30 mL of fresh PBS.

The following formulations were prepared, and are summarized in Table 1.

Experiment A (BU in 27.5 mg/mL collagen): The collagen was first concentrated to 120 mg/mL by vacuum drying for 2 hours. BU (16 mL, 120 mg) was then mixed with 4.76 g of collagen (total of 571.2 mg collagen). The resultant sample had a volume of approximately 21 mL, and a collagen and BU concentration of about 27.5 and 5.8 mg/mL respectively.

Experiment B (BU in 16 mg/mL collagen): BU (15 mL, 112.5 mg) was mixed with 5 mL (325 mg) of collagen. The resultant sample had a volume of approximately 20 mL, and a collagen and BU concentration of about 16 and 5.6 mg/mL respectively.

BU Control. BU (13 mL, 97.5 mg) was placed into the tubing without prior incubation at room temperature. The resultant sample had a volume of approximately 13 mL, and a BU concentration of 7.5 mg/mL.

Collagen Control: Collagen (5 mL, 325 mg) was placed into the tubing without prior incubation at room temperature. In this experiment only 10 mL of PBS was used.

TABLE 1

Formulations and In Vitro Study Conditions

| Description | A<br>Bupivacaine +<br>27.5 mg/mL<br>Collagen | B<br>Bupivacaine +<br>16 mg/mL<br>Collagen | BU<br>Bupivacaine<br>Solution<br>(control) | Collagen<br>Collagen<br>(control) |
|---|---|---|---|---|
| Concentration of Components in Final Composition ||||||
| Bupivacaine (mg/mL) | 5.8 | 5.6 | 7.5 | — |
| Collagen (mg/mL) | 27.5 | 16 | — | 65 |
| In Vitro Study Conditions ||||||
| Bupivacaine Dose (mg) | 120 | 112.5 | 98 | — |
| Total Formulation Mass (g) | 21 | 20 | 13 | 5 |
| PBS medium (mL) | 30 | 30 | 30 | 10 |

At each timepoint, the incremental and cumulative amount of bupivacaine released into the PBS was calculated. Percent released calculations were based on the initial amount of BU in the test sample. Average release rates were calculated and plotted as a function of t' (mid-point of the interval between timepoints). Differential scanning calorimetry (DSC) was also performed on the samples to investigate possible collagen/drug binding interactions.

Figure 1:
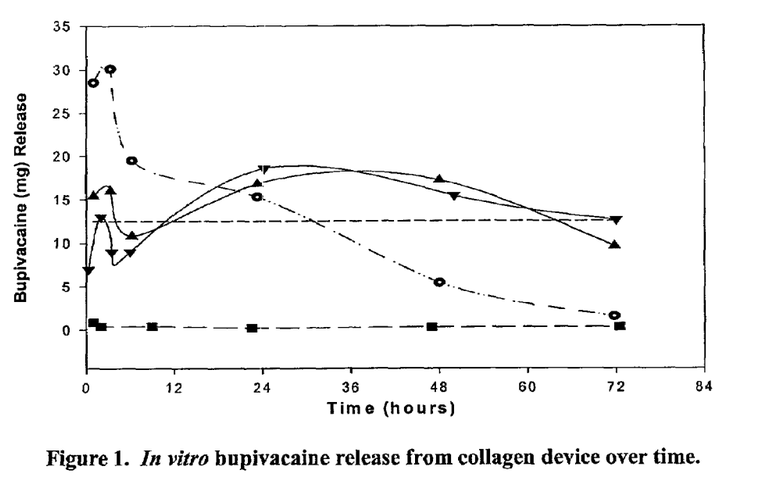
FIG. 1 shows the amount of bupivacaine released versus time, where (inverted triangle) indicates the release profile for Experiment A, (triangle) indicates the release profile for Experiment B, (circle) indicates the release profile of the bupivacaine control and (square) indicates the release profile of the collagen control, which is zero.
Figure 2:
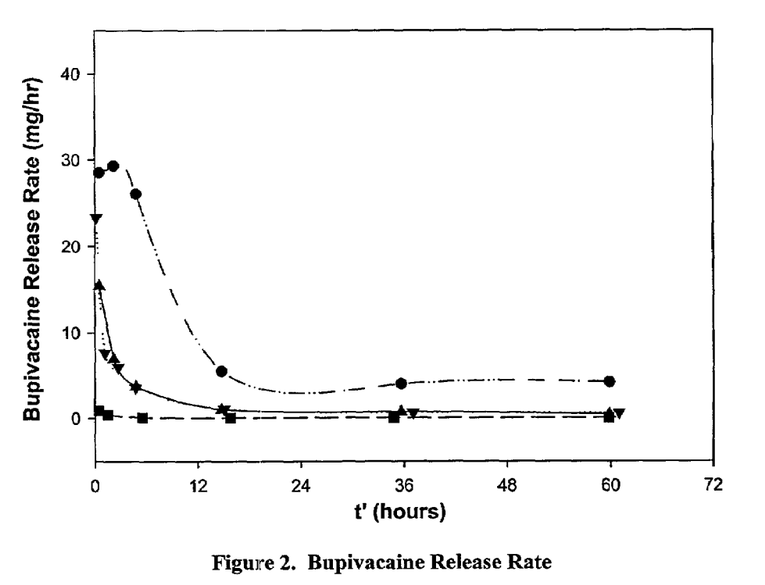
FIG. 2 shows the release rate (mg/hr) of bupivacaine released versus time, where (inverted triangle) indicates the release profile for Experiment A, (triangle) indicates the release rate for Experiment B, (circle) indicates the release rate of the bupivacaine control and (square) indicates the release rate of the collagen control, which is zero.
Figure 3:
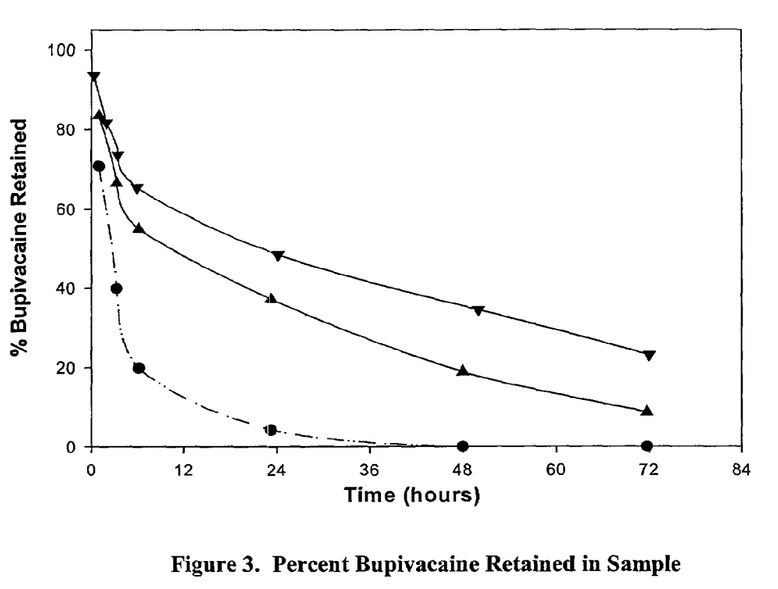
FIG. 3 shows the percentage of bupivacaine retained in the sample (calculated versus the starting amount of bupivacaine) versus time, where (inverted triangle) indicates the percentage of bupivacaine for Experiment A, (triangle) indicates the percentage of bupivacaine for Experiment B, and (circle) indicates the percentage of bupivacaine of the bupivacaine control.

Comparison of the amount of bupivacaine present in the dialysis sample at a given time (bupivacaine release, FIG. 1); the bupivacaine release rate (FIG. 2) and the % bupivacaine retained in the samples (FIG. 3) showed that the combination of the fibrillar non-crosslinked, atelopeptide Type I collagen and bupivacaine was effective in altering the release rate of soluble bupivacaine resulting in the controlled release of the bupivacaine over a 60–72 hour period.

These results are unexpected as the collagen described herein has not before been used to control the release of a pharmaceutical agent. Previous studies have used a variety of techniques including crosslinking of the collagen via radiation or chemical means to fabricate collagen matrices or other collagen formulations in order to achieve controlled release of pharmaceutical agents, that is, in order to use collagen as a means of drug delivery. As described here, the insoluble, non-crosslinked, fibrillar, atelopeptide Type I collagen merely requires mixing with the pharmaceutical agent and does not require elaborate or extensive preparation of the pharmaceutical agent or purified collagen to achieve controlled release of the pharmaceutical agent.

DSC results (data not shown) revealed a new peak prominent in the thermogram (melting at 45° C.) of the bupivacaine/collagen formulations suggesting that certain of the fibrils were disassembled by the BU to yield a population of fibrils of smaller diameter and indicating a structural change concomitant with the slowed release of the bupivacaine. The amount of bupivacaine released at a given time point, as shown by these in vitro results indicates that an effective amount of bupivacaine should be released in vivo to result in the treatment of post-surgical or incisional pain as described herein.

Example 2

A patient suffering from a meniscal tear in the knee joint is selected for arthroscopic repair of the meniscus. Arthroscopy to remove torn fragments and/or repair the meniscus is performed according to standard procedures. Following surgical repair of the meniscus but prior to closure of the incisions, 2 ml of a composition comprising 65 mg/ml bovine skin collagen in the presence and absence of lidocaine, bupivacaine or morphine at 20 mg/ml in phosphate buffered saline is administered into the knee joint via a catheter. The incisions are then sutured according to standard procedures.

Example 3

A patient suffering from a torn rotator cuff undergoes arthroscopic repair. Arthroscopy to reattach the torn rotator cuff is performed according to standard procedures. Following reattachment but prior to closure of the incisions, 2 ml of a composition comprising 65 mg/ml bovine skin collagen in the presence and absence of lidocaine, bupivacaine or morphine at 20 mg/ml in phosphate buffered saline is administered into the shoulder via a catheter. The incisions are then sutured according to standard procedures.

Example 4

A patient suffering from cartilage damage undergoes implantation of a repair matrix with or without autologous chondrocytes. Implantation of the repair matrix is performed according to standard procedures. Following implantation but prior to closure of the incisions, 2 ml of a composition comprising 65 mg/ml bovine skin collagen in the presence and absence of lidocaine, bupivacaine or morphine at 20 mg/ml in phosphate buffered saline is administered into the knee via a catheter. The incisions are then sutured according to standard procedures.

The invention claimed is:

1. A composition for the treatment of post-surgical articular or incisional pain or discomfort consisting essentially of an aqueous dispersion of insoluble non-crosslinked type I fibrillar atelopeptide collagen and an anesthetic; wherein the composition is formulated to release an effective amount of the anesthetic from the collagen for at least 48 hours, wherein the collagen and the anesthetic are in a ratio of from about 0.5:1 to about 10:1, and wherein the melting temperature of the composition is from about 42° C. to about 46° C.

2. The composition of claim 1, wherein the anesthetic is soluble in the dispersion.

3. The composition of claim 1, wherein the composition is formulated to release an effective amount of the anesthetic from the collagen for at least 72 hours.

4. The composition of claim 1, wherein the collagen consists essentially of at least 95% Type I non-crosslinked fibrillar atelopeptide collagen.

5. The composition of claim 1, wherein the collagen is less than 5% Type III collagen.

6. The composition of claim 1, wherein the anesthetic is bupivacaine, lidocaine, procaine, procainamide, tetracaine, mepivacaine, or etidocaine.

7. The composition of claim 1, wherein the collagen is human collagen or bovine dermal collagen.

8. The composition of claim 1, wherein a total amount of anesthetic released is from about 5 mg to 1 g.

9. The composition of claim 1, further comprising one or more pharmaceutically acceptable excipient(s).

10. The composition of claim 1, wherein the melting temperature of the composition is about 45° C.

11. The composition of claim 1, wherein the collagen and the anesthetic are in a ratio of from about 1:1 to about 5:1.

12. The composition of claim 11, wherein the collagen and the anesthetic are in a ratio of from about 1:1.

13. The composition of claim 1, wherein the anesthetic concentration is about 4–30 mg/ml.

14. The composition of claim 13, wherein the anesthetic concentration is from about 4 mg/ml to about 10 mg/ml.

15. The composition of claim 1, wherein the effective amount of anesthetic released is from about 2–15 mg per day.

16. The composition of claim 15, wherein the effective amount of anesthetic released is about 10 mg per day.

17. The composition of claim 1, wherein the collagen concentration is from about 3 mg/ml to about 100 mg/ml.

18. The composition of claim 17, wherein the collagen concentration is from about 65 mg/ml.

19. The composition of claim 17, wherein the collagen concentration is from about 16 mg/ml to about 28 mg/ml.

20. A composition for the treatment of post-surgical articular or incisional pain or discomfort consisting essentially of an aqueous dispersion of insoluble non-crosslinked type I fibrillar atelopeptide collagen and bupivacaine; wherein the composition is formulated to release an effective amount of the bupivacaine from the collagen for at least 48 hours, wherein the collagen and bupivacaine are in a ratio of from about 0.5:1 to about 10:1, and wherein the melting temperature of the composition is from about 42° C. to about 46° C.

21. The composition of claim 20, wherein the bupivacaine is soluble in the dispersion.

22. The composition of claim 20, wherein the composition is formulated to release an effective amount of bupivacaine from the collagen for at least 72 hours.

23. The composition of claim 20, wherein the collagen consists essentially of at least 95% Type I non-crosslinked fibrillar atelopeptide collagen.

24. The composition of claim 20, wherein the collagen is less than 5% Type III collagen.

25. The composition of claim 20, wherein a total amount of bupivacaine released is from 5 mg to 1 g.

26. The composition of claim 20, wherein the effective amount of bupivacaine released is about 2–15 mg per day.

27. The composition of claim 20, further comprising one or more pharmaceutically acceptable excipients.

28. The composition of claim 20, wherein the melting temperature of the composition is about 45° C.

29. The composition of claim 20, wherein the collagen and bupivacaine are in a ratio of from about 1:1 to about 5:1.

30. The composition of claim 29, wherein the collagen and bupivacaine are in a ratio of from about 3.1 to about 4.7:1.

31. The composition of claim 20, wherein the bupivacaine concentration of is about 4–30 mg/ml.

32. The composition of claim 31, wherein the bupivacaine concentration is from about 4 mg/ml to about 10 mg/ml.

33. The composition of claim 20, wherein the collagen concentration is from about 10 mg/ml to about 100 mg/ml.

34. The composition of claim 33, wherein the collagen concentration is about 65 mg/ml.

35. The composition of claim 33, wherein the collagen concentration is from about 16 mg/ml to about 28 mg/ml.

36. A method for the treatment of post-surgical pain or discomfort in a joint(s) comprising the step of intra-articularly administering to a joint(s) in a patient a composition consisting essentially of an aqueous dispersion of insoluble non-crosslinked Type I fibrillar atelopeptide collagen and an anesthetic; wherein the composition is formulated to release an effective amount of the anesthetic from the collagen for at least 48 hours, wherein the collagen and the anesthetic are in a ratio of from about 0.5:1 to about 10:1, wherein melting temperature of the composition is from about 42° C. to about 46° C., and wherein the composition is administered before, during or after a surgical procedure.

37. The method of claim 36, wherein the composition is administered during the surgical procedure.

38. The method of claim 36, wherein the composition is administered after the surgical procedure.

39. The method of claim 36, wherein the composition is administered via a catheter.

40. The method of claim 36, wherein the surgical procedure is arthroscopy, arthrotomy, implantation of chondrocytes, implantation of cartilage, partial joint arthroplasty or total joint arthroplasty.

41. The method of claim 36, wherein the composition is formulated to release an effective amount of the anesthetic from the collagen for at least 72 hours.

42. The method of claim 36, wherein the collagen and the anesthetic are in a ratio of from about 1:1 to about 5:1.

43. The method of claim 36, wherein the collagen consists essentially of at least 95% Type I non-crosslinked fibrillar atelopeptide collagen.

44. The method of claim 36, wherein the collagen is less than 5% Type III collagen.

45. The method of claim 36, wherein the anesthetic is bupivacaine, lidocaine, procaine, procainamide, tetracaine, mepivacaine, or etidocaine.

46. The method of claim 36, wherein the collagen concentration is from about 3 mg/ml to about 100 mg/ml.

47. The method of claim 36, wherein a total amount of anesthetic released is from about 5 mg to 1 g.

48. The method of claim 36, wherein the amount of composition administered is greater than 2 mL.

49. The method of claim 36, wherein the composition further includes one or more pharmaceutically acceptable excipient(s).

50. The method of claim 36, wherein the joint is a knee, shoulder, ankle, hip, wrist, elbow or temporomandibular joint.

51. The method of claim 50, wherein the joint is a knee.

52. The method of claim 36, wherein the patient is a human or veterinary patient.

53. The method of claim 52, wherein the patient is a human.

54. The method of claim 36, wherein the composition is administered before the surgical procedure.

55. The method of claim 54, wherein the method further comprises the step of at least one additional administration of the composition during or after the surgical procedure.

56. The method of claim 36, wherein the surgical procedure is used in the treatment of a condition selected from the group consisting of meniscal injury, anterior cruciate ligament injury, rotator cuff injury, carpal tunnel syndrome, synovitis, chondromalacia, patellar tendon rupture, tibial tubercle fracture, loose bodies of bone or cartilage, osteochondritis dissecans, adhesive capsulitis, impingement syndrome, shoulder dislocation, Dupuytren's syndrome, scaphoid fracture, stenosing tenosynovitis, lateral facet syndrome, anterior patello-femoral pain syndrome, lateral pressure syndrome, malalignment syndrome, and maltracking syndrome.

57. The method of claim 56, wherein the condition is not a degenerative articular process.

58. The method of claim 36, wherein the anesthetic concentration is about 4–30 mg/ml.

59. The method of claim 58, wherein the anesthetic concentration is from about 4 mg/ml to about 10 mg/ml.

60. The method of claim 36, wherein the effective amount of anesthetic released is from about 2–15 mg per day.

61. The method of claim 60, wherein the effective amount of anesthetic released is about 10 mg per day.

62. A method for the treatment of post-surgical pain or discomfort associated with one or more incisions comprising the step administering to a patient's incision(s) a composition consisting essentially of an aqueous dispersion of insoluble non-crosslinked type I fibrillar atelopeptide collagen and an anesthetic; wherein the composition is formulated to release an effective amount of the anesthetic from the collagen for at least 48 hours, wherein the collagen and the anesthetic are in a ratio of from about 0.5:1 to about 10:1, wherein the melting temperature of the composition is from about 42° C. to about 46° C., and wherein the composition is administered before, during or after a surgical procedure.

63. The method of claim 62, wherein the composition is administered via injection.

64. The method of claim 62, wherein the composition is administered during the surgical procedure.

65. The method of claim 62, wherein the composition is administered after the surgical procedure.

66. The method of claim 62, wherein the composition is administered via a catheter.

67. The method of claim 62, wherein the anesthetic is bupivacaine.

68. The method of claim 62, wherein the surgical procedure is an abdominal, spinal or breast operation.

69. The method of claim 68, wherein the abdominal operation is a cesarean birth, hernia repair, or hysterectomy.

70. The method of claim 62, wherein the patient is a human or veterinary patient.

71. The method of claim 70, wherein the patient is a human.

72. The method of claim 62, wherein the composition is administered before the surgical procedure.

73. The method of claim 72, wherein the method further comprises the step of at least one additional administration of the composition during or after the surgical procedure.

74. A method for the treatment of post-surgical pain or discomfort in a joint(s) comprising the step of intra-articularly administering to a joint(s) in a patient a composition consisting essentially of an aqueous dispersion of insoluble non-crosslinked type I fibrillar atelopeptide collagen and bupivacaine, wherein the composition is formulated to release an effective amount of the bupivacaine from the collagen for at least 48 hours, wherein the collagen and bupivacaine are in a ratio of from about 0.5:1 to about 10:1, wherein the melting temperature of the composition is from about 42° C. to about 46° C., and wherein the composition is administered before, during or after a surgical procedure.

75. The method of claim 74, wherein the composition is administered during the surgical procedure.

76. The method of claim 74, wherein the composition is administered after the surgical procedure.

77. The method of claim 74, wherein the composition is administered via a catheter.

78. The method of claim 74, wherein the surgical procedure is arthroscopy, arthrotomy, implantation of chondrocytes, implantation of cartilage, partial joint arthroplasty or total joint arthroplasty.

79. The method of claim 74, wherein the surgical procedure is used in the treatment of a condition selected from the group consisting of meniscal injury, anterior cruciate ligament injury, rotator cuff injury, carpal tunnel syndrome, synovitis, chondromalacia, patellar tendon rupture, tibial tubercle fracture, loose bodies of bone or cartilage, osteochondritis dissecans, adhesive capsulitis, impingement syndrome, shoulder dislocation, Dupuytren's syndrome, scaphoid fracture, stenosing tenosynovitis, lateral facet syndrome, anterior patello-femoral pain syndrome, lateral pressure syndrome, malalignment syndrome, and maltracking syndrome.

80. The method of claim 74, wherein the composition is formulated to release an effective amount of bupivacaine from the collagen for at least 72 hours.

81. The method of claim 74, wherein the collagen and bupivacaine are in a ratio of from about 1:1 to about 5:1.

82. The method of claim 74, wherein the collagen consists essentially of at least 95% Type I non-crosslinked fibrillar atelopeptide collagen.

83. The method of claim 74, wherein the collagen is less than 5% Type III collagen.

84. The method of claim 74, wherein the collagen is human collagen or bovine dermal collagen.

85. The method of claim 74, wherein the collagen concentration is from about 3 mg/ml to about 100 mg/ml.

86. The method of claim 74, wherein a total amount of bupivacaine released is from about 5 mg to 1 g.

87. The method of claim 74, wherein the amount of composition administered is greater than 2 mL.

88. The method of claim 74, wherein the composition further includes one or more pharmaceutically acceptable excipient(s).

89. The method of claim 74, wherein the joint is a knee, shoulder, ankle, hip, wrist, elbow or temporomandibular joint.

90. The method of claim 89, wherein the joint is a knee.

91. The method of claim 74, wherein the patient is a human or veterinary patient.

92. The method of claim 91, wherein the patient is a human.

93. The method of claim 74, wherein the composition is administered before the surgical procedure.

94. The method of claim 93, wherein the method further comprises the step of at least one additional administration of the composition during or after the surgical procedure.

95. The method of claim 74, wherein the bupivacaine concentration is about 4–30 mg/ml.

96. The method of claim 95, wherein the bupivacaine concentration is from about 4 mg/ml to about 10 mg/ml.

97. The method of claim 74, wherein the effective amount of bupivacaine released is from about 2–15 mg per day.

98. The method of claim 74, wherein the effective amount of bupivacaine released is about 10 mg per day.

* * * * *

UNITED STATES PATENT AND TRADEMARK OFFICE
CERTIFICATE OF CORRECTION

| | |
|---|---|
| PATENT NO. | : 7,119,062 B1 |
| APPLICATION NO. | : 10/082443 |
| DATED | : October 10, 2006 |
| INVENTOR(S) | : Mark R. Alvis et al. |

It is certified that error appears in the above-identified patent and that said Letters Patent is hereby corrected as shown below:

In claim 12, column 17, line 63, please replace "and the anesthetic are in a ratio of from about 1:1" with --and the anesthetic are in a ratio of about 1:1--; and In claim 18, column 18, line 9, please replace "concentration is from about 65 mg/ml." with --concentration is about 65 mg/ml.--; and In claim 30, column 18, line 44, please replace "are in a ratio of from about 3.1 to about 4.7:1." with --are in a ratio of from about 3:1 to about 4.7:1.--; and In claim 31, column 18, line 47, please replace "concentration of is about 4-30 mg/ml." with --concentration is about 4-30 mg/ml.--; and In claim 74, column 20, line 41, please replace "non-crosslinked type I" with --non-crosslinked Type I--; and In claim 98, column 22, line 21, please replace "The method of claim 74" with --The method of claim 97--

Signed and Sealed this

Sixteenth Day of December, 2008

JON W. DUDAS
*Director of the United States Patent and Trademark Office*